(12) United States Patent
Goodman

(10) Patent No.: US 10,849,759 B2
(45) Date of Patent: Dec. 1, 2020

(54) CERAMIC MULTI-HOODED ENARTHRODIAL JOINT IMPLANT

(71) Applicant: Floyd G. Goodman, Williamston, MI (US)

(72) Inventor: Floyd G. Goodman, Williamston, MI (US)

(*) Notice: Subject to any disclaimer, the term of this patent is extended or adjusted under 35 U.S.C. 154(b) by 44 days.

(21) Appl. No.: 15/932,520

(22) Filed: Mar. 10, 2018

(65) Prior Publication Data

US 2018/0256342 A1  Sep. 13, 2018

Related U.S. Application Data

(60) Provisional application No. 62/601,178, filed on Mar. 13, 2017.

(51) Int. Cl.
*A61F 2/32* (2006.01)
*A61F 2/36* (2006.01)
(Continued)

(52) U.S. Cl.
CPC .................. *A61F 2/32* (2013.01); *A61F 2/34* (2013.01); *A61F 2/3601* (2013.01); *A61F 2/4081* (2013.01); *A61F 2002/30448* (2013.01); *A61F 2002/30578* (2013.01); *A61F 2002/3233* (2013.01); *A61F 2002/3241* (2013.01);
(Continued)

(58) Field of Classification Search
CPC .. A61F 2/32; A61F 2/3609; A61F 2/36; A61F 2002/3617; A61F 2002/3623; A61F 2/34; A61F 2/3601; A61F 2/3607; A61F 2/30739; A61F 2002/365; A61F 2002/3654; A61F 2002/4074; A61F 2002/4037; A61F 2002/30294; A61F 2002/30329; A61F 2002/30332; A61F 2002/30349; A61F 2002/3035
See application file for complete search history.

(56) References Cited

U.S. PATENT DOCUMENTS 5,462,575 A  10/1995  Del Corso
5,624,464 A   4/1997  Wagner et al.
(Continued)

OTHER PUBLICATIONS

Nielsen, Reply and Amendment with Claims and Remarks filed in Ries, U.S. Appl. No. 15/282,738, dated Oct. 27, 2017 A.D.
(Continued)

*Primary Examiner* — Alvin J Stewart
(74) *Attorney, Agent, or Firm* — Christopher John Rudy

(57) ABSTRACT

Multi-hooded enarthrodial joint implant has a ceramic articulating cup including a ceramic head-receiving cup having an articular surface upon which a head of a joint can articulate, and which, in general, has a margin generally about a hemisphere more or less and at least two hoods that are marginally extended continuations of superior one-half or so of cup containment of a sufficient magnitude to reduce an overall dimension of socket outlet to less than a hemisphere, which can embrace and contain the head. The head is made of ceramic and has a truncated generally circular cross section, a truncated surface with a feature for attachment of the stem, and an opposing articular surface for articulation against the articular surface of the ceramic head-receiving cup. As an ensemble, the cup is combined with the head, typically with a stem, for a total joint implant.

15 Claims, 4 Drawing Sheets

(51) Int. Cl.
*A61F 2/34* (2006.01)
*A61F 2/40* (2006.01)
*A61F 2/30* (2006.01)

(52) U.S. Cl.
CPC . *A61F 2002/349* (2013.01); *A61F 2002/3448* (2013.01); *A61F 2002/3493* (2013.01); *A61F 2230/0076* (2013.01); *A61F 2310/00017* (2013.01); *A61F 2310/00023* (2013.01); *A61F 2310/00029* (2013.01); *A61F 2310/00047* (2013.01); *A61F 2310/00053* (2013.01); *A61F 2310/00059* (2013.01); *A61F 2310/00101* (2013.01); *A61F 2310/00179* (2013.01); *A61F 2310/00197* (2013.01); *A61F 2310/00203* (2013.01); *A61F 2310/00239* (2013.01); *A61F 2310/00317* (2013.01)

(56) References Cited

U.S. PATENT DOCUMENTS

| | | | |
|---|---|---|---|
| 5,871,547 A | 2/1999 | Abouaf et al. | |
| 6,093,208 A | 7/2000 | Tian | |
| 6,096,083 A | 8/2000 | Keller et al. | |
| 6,299,647 B1 | 10/2001 | Townley | |
| 6,319,285 B1 | 11/2001 | Chamier et al. | |
| 6,682,567 B1 | 1/2004 | Schroeder | |
| 6,881,229 B2 | 4/2005 | Khandkar et al. | |
| 7,335,231 B2* | 2/2008 | McLean | A61F 2/32 623/22.15 |
| 7,455,694 B2* | 11/2008 | Epaules | A61F 2/32 623/22.15 |
| 7,520,902 B2 | 4/2009 | Deloge' et al. | |
| 7,682,398 B2 | 3/2010 | Croxton et al. | |
| 7,695,521 B2 | 4/2010 | Ely et al. | |
| 7,780,739 B2* | 8/2010 | Lakin | A61F 2/32 623/22.17 |
| 7,892,289 B2 | 2/2011 | Serafin, Jr. et al. | |
| 7,981,160 B1* | 7/2011 | Serafin, Jr. | A61F 2/32 623/22.25 |
| 8,679,187 B2 | 3/2014 | Allen et al. | |
| 8,801,797 B2 | 8/2014 | Imhof | |
| 8,834,576 B1 | 9/2014 | Serafin, Jr. | |
| 9,078,754 B1 | 7/2015 | Serafin, Jr. et al. | |
| 9,173,740 B2 | 11/2015 | Gradel | |
| 9,259,508 B2* | 2/2016 | Serafin, Jr. | A61L 27/10 |
| 9,272,095 B2* | 3/2016 | Felts | A61M 5/3129 |
| 9,308,674 B1* | 4/2016 | Serafin, Jr. | B29C 31/02 |
| 9,427,322 B1 | 8/2016 | Serafin, Jr. | |
| 9,561,111 B1* | 2/2017 | Goodman | A61F 2/40 |
| 9,907,661 B2 | 3/2018 | Ries | |
| 2002/0013625 A1 | 1/2002 | Abouaf et al. | |
| 2002/0031675 A1 | 3/2002 | Cales et al. | |
| 2002/0116068 A1* | 8/2002 | McLean | A61F 2/32 623/22.15 |
| 2003/0171817 A1* | 9/2003 | Rambert | A61F 2/32 623/22.17 |
| 2003/0216732 A1* | 11/2003 | Truckai | A61B 18/14 606/49 |
| 2007/0191961 A1* | 8/2007 | Aux Epaules | A61F 2/32 623/22.18 |
| 2008/0074643 A1* | 3/2008 | Chen | A61C 7/00 356/32 |
| 2009/0093887 A1 | 4/2009 | Walter et al. | |
| 2010/0076566 A1 | 3/2010 | Serafin, Jr. et al. | |
| 2010/0087930 A1 | 4/2010 | Tuke et al. | |
| 2011/0243650 A1* | 10/2011 | Linares | A61F 2/30771 403/122 |
| 2011/0257757 A1* | 10/2011 | Popoola | A61F 2/32 623/22.15 |
| 2012/0252709 A1* | 10/2012 | Felts | A61M 5/3129 508/100 |
| 2013/0261761 A1* | 10/2013 | Whitaker | A61F 2/32 623/22.16 |
| 2014/0069202 A1* | 3/2014 | Fisk | A61M 5/3129 73/762 |
| 2014/0128988 A1* | 5/2014 | Muratoglu | A61F 2/30 623/23.11 |
| 2017/0202671 A1* | 7/2017 | Ries | A61F 2/4637 |

OTHER PUBLICATIONS

Watkins, Office action Issued in Ries, U.S. Appl. No. 15/282,738, dated Aug. 1, 2017 A.D.

* cited by examiner

CERAMIC MULTI-HOODED ENARTHRODIAL JOINT IMPLANT

This claims benefits under 35 USC 119(e) of provisional patent application No. US 62/601,178 filed on Mar. 13, 2017 A.D. The specification of that application, to include drawings, is incorporated herein by reference in its entirety.

FIELD AND PURVIEW OF THE INVENTION

This concerns a multi-hooded enarthrodial joint implant with a ceramic articulating cup, separately, as an ensemble or kit, or part thereof. For example, the implant may be an ensemble for a hip or a shoulder with a double-hooded ceramic acetabular or glenoid cup and a modular femoral or humeral stem with a truncated ball head of matching or complimentary ceramic.

BACKGROUND TO THE INVENTION

Various enarthrodial joint implants are known. Among those some have two or more "hoods," also known as "veils," on a portion of an articulating cup for ameliorating dislocation of an inserted ball of the joint. See, e.g., Serafin, Jr. et al., U.S. Pat. No. 7,981,160 B1. The acetabular cup of that implant is fitted with a suitably resilient, tough material that may include a plastic such as a polyurethane or polyolefin and so forth, for example, a polyethylene, say, an ultra high molecular weight polyethylene (UHMWPE). In order to assist in retaining the ball head of the femoral component in the cup, a securing member provides for resistance against outward displacement of hoods of the cup. A drawback may ensue with employment of such materials as UHMWPE or other resilient materials for the cup in that, when implanted, they may leave wear debris that may engender osteolytic loosening of the implant. In address of plastic wear debris, some enarthrodial joint art employs as a wear couple a hard-surface-on hard-surface articulation such as a metal-on-metal, metal-on-ceramic, or ceramic-on-ceramic articulation. The metal-containing wear couples themselves form metal wear debris, which may be targeted for blame in osteolytic loosening of implants and in other biologic phenomena such as severe tissue discoloration, and possible allergic reaction. Accordingly, ceramic wear couples may be employed to lower propensities for osteolytic loosening of an implant caused by wear debris particles. Such rigid, hard materials, however, are not without drawback, among these being inflexibility. Thus, hard enarthrodial joint wear couples typically are limited to configurations unconstrained from dislocation save that provided by healthy tissue, which may not be present about a surgical implant site; or, if constrained from dislocation, are constrained with implant structures that are bulky, cumbersome or complex mechanically, or limit more full and natural range of motion, with some of these retaining a plastic cup such as of UHMWPE. Certain implants are made with notable materials, and some implants are coated, notably with porous or other bone-ingrowth engendering coatings. Compare, Del Corso, U.S. Pat. No. 5,462,575; Abouaf et al., U.S. Pat. No. 5,871,547; Tian, U.S. Pat. No. 6,093,208; Keller et al., U.S. Pat. No. 6,096,083; Townley, U.S. Pat. No. 6,299,647 B1; Chamier et al., U.S. Pat. No. 6,319,285 B1; Schroeder, U.S. Pat. No. 6,682,567 B1; Khandkar et al., U.S. Pat. No. 6,881,229 B2; McLean, U.S. Pat. No. 7,335,231 B2; Epaules et al., U.S. Pat. No. 7,455,694 B2; Croxton et al., U.S. Pat. No. 7,682,398 B2; Ely et al., U.S. Pat. No. 7,695,521 B2; Lakin et al., U.S. Pat. No. 7,780,739 B2; Serafin, Jr. et al., U.S. Pat. No. 7,892,289 B2; Allen et al., U.S. Pat. No. 8,679,187 B2; Imhof, U.S. Pat. No. 8,801,797 B2; Serafin, Jr., U.S. Pat. No. 8,834,576 B1; Serafin, Jr. et al., U.S. Pat. No. 9,078,754 B1; Gradel, U.S. Pat. No. 9,173,740 B2; Serafin, Jr. et al., U.S. Pat. No. 9,259,508 B2; Serafin, Jr. et al., U.S. Pat. No. 9,308,674 B1; Serafin, Jr., U.S. Pat. No. 9,427,322 B1; Goodman, U.S. Pat. No. 9,561,111 B1; Abouaf et al., Pub. No. US 2002/0013625 A1; Cales et al., Pub. No. US 2002/0031675 A1; Walter et al., Pub. No. US 2009/0093887 A1; Serafin, Jr. et al., Pub. No. US 2010/0076566 A1; Tuke et al., Pub. No. US 2010/0087930 A1.

It would be desirable to improve upon the art and/or provide it with an alternative. It would be desirable to provide an enarthrodial joint implant that ameliorates or solves multiple drawbacks in the art such as dislocation, wear debris production, and possible allergic reaction.

A FULL DISCLOSURE OF THE INVENTION

Provided hereby is a multi-hooded enarthrodial joint implant with a ceramic articulating cup comprising a ceramic head-receiving cup having an articular surface upon which a head of a joint can articulate, and which, in general, has a margin generally about a hemisphere more or less and at least two hoods that are marginally extended continuations of superior one-half or so of cup containment of a sufficient magnitude to reduce an overall dimension of socket outlet to less than a hemisphere, which can embrace and contain the head. In an ensemble, the cup is combined with a modular head and stem arrangement for a total joint implant, in which the head is of ceramic and has a truncated generally (i.e., of reasonable inclusion) circular cross section, a truncated surface with a feature for attachment of the stem, and an opposing articular surface for articulation against the articular surface of the ceramic head-receiving cup. The head may be or contain a sphere, spheroid, ellipsoid, truncated rod, and so forth and the like element, at least in substantial part. Optionally provided also can be a securing member that provides for resistance against any likelihood, if any, of cracking, fracture, or other failure of the ceramic such as by an application of unusually great outwardly displacing force. Additional optional feature(s) may be provided also such as a bone-interfacing coating; a ring, which may include, for example, a bone-interfacing coating; an outer backing shell for the cup; and so forth.

The invention is useful in arthroplasty.

Significantly, by the invention, problems in the art are ameliorated if not overcome. In particular, total joint implants are made dramatically more secure by resistance to dislocation and reduction in wear debris, which may reduce a propensity for osteolytic loosening of the implant. Also, particularly when metal is avoided, certain allergic reactions and/or potential for particulate metal reactivity may be reduced or avoided.

Numerous further advantages attend the invention.

The drawings form part of the specification hereof With respect to the drawings, which are not necessarily drawn to scale, the following is briefly noted:

Figure 1:
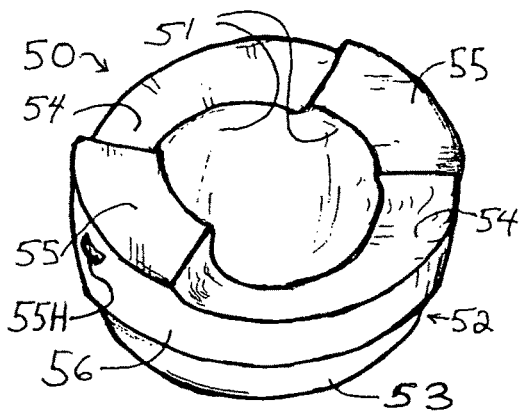
FIG. 1 is a perspective view of a ceramic multi-hooded enarthrodial joint implant cup of the invention for an ensemble therewith, the same being embodied as a double-hooded ceramic acetabular cup for a total conventional hip replacement implant.
Figure 2:
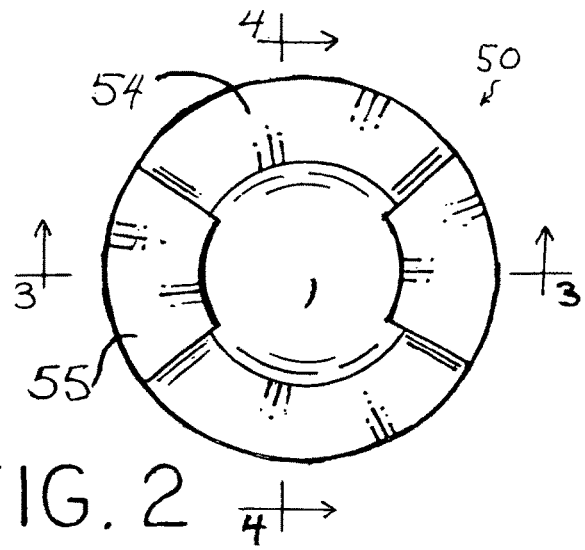
FIG. 2 is a "front" view of the cup of FIG. 1.
Figure 3:
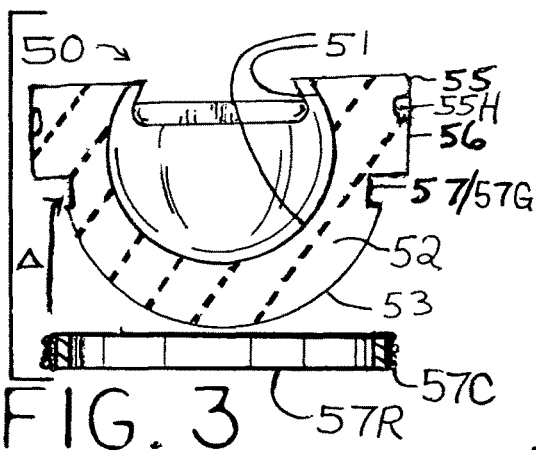
FIG. 3 is a sectional view of the cup of FIG. 1, taken along 3-3 of FIG. 2.
Figure 4:
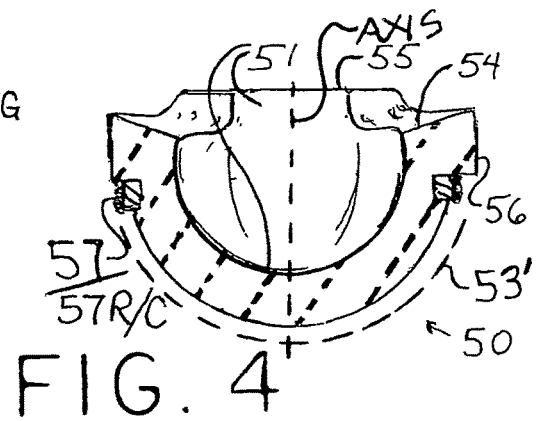
FIG. 4 is a sectional view of the cup of FIG. 1, taken along 4-4 of FIG. 2, which is normal to 3-3 of FIG. 2.

The invention can be further understood by the following additional detail, which, as with the foregoing, may be read in view of the drawings. Such is to be taken in an illustrative and not necessarily limiting sense.

The principles of the invention can be applied to provide a ceramic multi-hooded enarthrodial joint implant cup ensemble, or parts thereof, for any suitable enarthrodial joint, or other generally corresponding pivoting joint, to include the hip, shoulder, thumb or finger. The hip and shoulder are illustratively depicted.

Any suitable material may be employed. Generally, materials are biocompatible. Thus, material for the cup and any corresponding modular head for receipt in the cup is selected from any suitable ceramics to include ceramics as an alumina, a silicon nitride, and/or a zirconia, especially magnesium oxide stabilized transformation toughened zirconia (MgO-TTZ) as, for example, stabilized by about from 3% to 3 ½% by weight magnesium oxide, and material for the securing member, and any security enhancing fastener, may be selected from suitably rigid, strong materials that may include such plastics as nylons, polycarbonates or epoxies; such; such ceramics as aforesaid; such metals or alloys as titanium, cobalt, stainless steel, titanium-vanadium-aluminum, cobalt-chrome, and so forth. Additional component parts, if present, are made of suitable materials. For instance, a backing shell may be made of a suitable ceramic or metal such as aforesaid, for example, 6-4 ELI titanium alloy; a stem for the modular head and stem assembly may be made of a suitable ceramic and/or metal, for example, a cobalt-chrome alloy, stainless steel, and so forth.

The hoods of the cup embrace the head of a joint greater than the circular cross section, for example, as a truncated spherical ball head greater than a hemisphere, in general, at least about their areas of contact with the head. In other words, in general, the hoods are marginally extended continuations of the superior one-half or so of the cup containment of a sufficient magnitude to reduce the overall dimension of the socket outlet to less than a half a circle in cross section, say again, a hemisphere in the case of a truncated spherical ball head. The truncated head is slid sideways into the cup into the embrace of the hoods. After insertion of the head into the hooded cup, the head is rotated in relation to the cup so as to bring its truncated surface into position to have the corresponding stem attached. Then any securing member may be brought into position.

More than one hood is required in the practice of the present invention. Thus, for instance, two, three, four or more hoods may be employed, say, with two opposing hoods; with three hoods equidistant about the margin of the cup and margin segments and hoods having about the same arc lengths, or with hoods having less of an arc length than the margins such as from about ½ to ¾ of the arc length of the margins; with three hoods not equidistant about the margin and themselves having the same arc lengths, or with one having a larger arc length opposed by two with lesser arc lengths; with four hoods equidistant about the margin and margin segments and hoods having about the same arc lengths, or with hoods having less of an arc length than the margins; with four hoods about the margin, two of the hoods in a set opposing two of the hoods in another set with greater margins between the two sets of hoods than between each hood in a set, or in an asymmetric arrangement, and so forth. Advantageously, the ceramic multi-hooded enarthrodial joint implant is embodied as a double-hooded cup.

Any suitable configuration for the modular head and stem may be employed. In general, however, there is a head component separate from but attachable with a stem component. The attachment may be carried out by any suitable method or means such as one or more of gluing, screwing, friction fitting, pressure fitting, and so forth. A tapered receptacle into which a corresponding trunnion is inserted may be employed. For example, the head may contain the tapered receptacle, for example, a conically or frustoconically tapered receptacle, with the corresponding trunnion being provided on a stem extremity. A self-locking taper such as, for example, a Morse taper, may be employed.

As optional further securement, the securing member provides for resistance against any likelihood, if any, of cracking, fracture, or other failure of the ceramic such as by an application of unusually great outwardly displacing force. Preferably, the securing member secures at least two hoods, and may secure each of the hoods present with the cup. The securing member may take any suitable form. For example, it may take the form of a ring or a U-shaped or a horseshoe-shaped member.

Additional parts or components may be present. For instance, a backing shell may be present, into which the cup is inserted, or an implant bone insert such as in Serafin, Jr. et al., U.S. Pat. No. 7,892,289 B2, may be provided to the head.

With respect to the drawings, ceramic joint head 20 articulates within multi-hooded enarthrodial joint implant cup 50 in ensemble 100. Securing member 70 may be present.

The joint head 20—made, for instance, of a ceramic such as an alumina or a zirconia, for example, MgO-TTZ such as in Serafin, Jr. et al., U.S. Pat. No. 9,259,508 B2,—is in a shape of a truncated sphere; has articulation surface 20A, blind frustoconical hole 20H with Morse taper in truncated surface 20S and central truncation distance 20T greater than the head radius, say, about from 60%, 65% or 70% to 75%, 80% or 85% of the head diameter; and is connectable to stem 21. For instance, the stem 21—made, say, of a forged alloy of cobalt-chromium to ASTM F-799 specifications, or of a non-magnetic cobalt-chromium-molybdenum alloy as a wrought powder metallurgy product such as BioDur® CCM Plus alloy (Carpenter Technology Corp.), U.S. Pat. No. 5,462,575, which can be configured such as in Serafin, Jr., U.S. Pat. No. 9,427,322 B1—includes trunnion 21T having corresponding Morse taper, which is inserted into the hole 20H of the head 20 for insertion into the medullary canal of the resected upper femur of a human patient.

Figure 5:
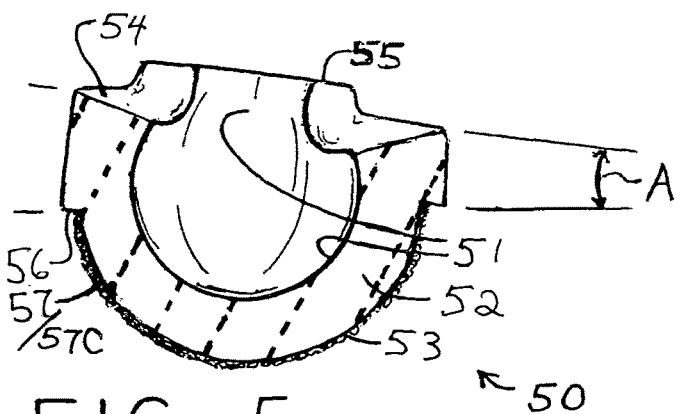
FIG. 5 is a sectional view of another ceramic multi-hooded enarthrodial joint implant cup of the invention for an ensemble therewith, the same being embodied as a double-hooded ceramic acetabular cup for a total conventional hip replacement implant, and having angular displacement of the margin and hoods. Compare, FIG. 4.
Figure 6:
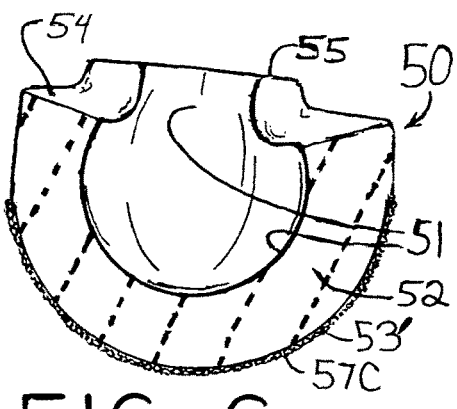
FIG. 6 is a sectional view of another ceramic multi-hooded enarthrodial joint implant cup of the invention for an ensemble therewith, embodied as a double-hooded ceramic acetabular cup for a total conventional hip replacement implant, and having angular displacement of the margin and hoods. Compare, FIG. 5.
Figure 7:
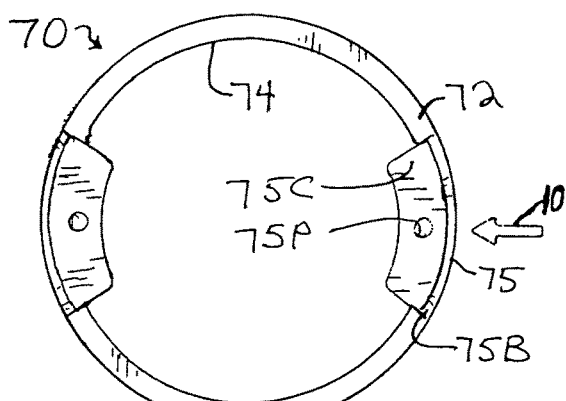
FIG. 7 is a "front" view of a securing member of the invention for an ensemble therewith, the same being embodied as a 6-4 ELI titanium alloy ring.
Figure 8:
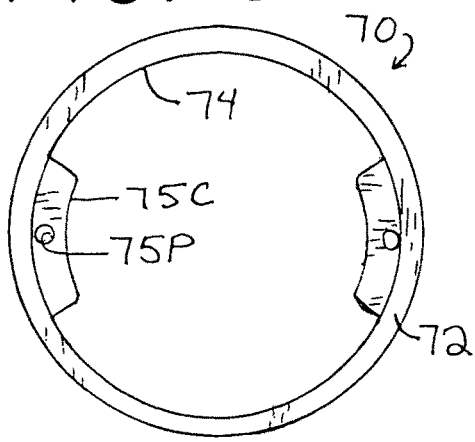
FIG. 8 is a "rear" view of the securing member of FIG. 7.
Figure 9:
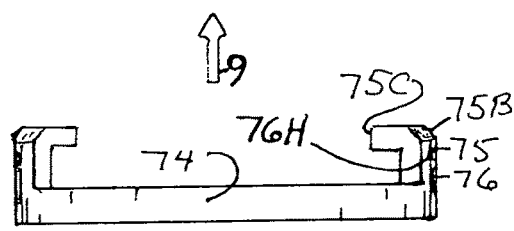
FIG. 9 is a "side" view of the securing member of FIG. 7, taken along arrow 9 in FIG. 7.
Figure 10:
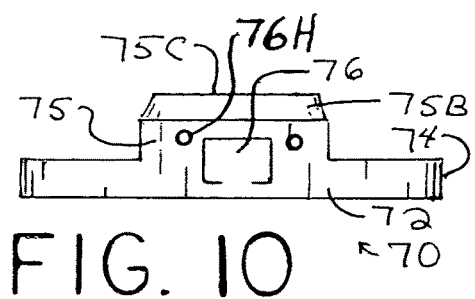
FIG. 10 is a "side" view of the securing member of FIG. 7, taken along arrow 10, which is normal to arrow 9 in FIG. 7.
Figure 11:
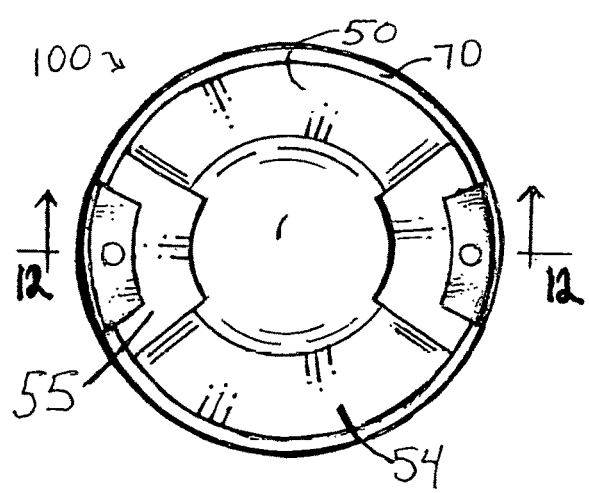
FIG. 11 is a "top" view of an ensemble of the invention, which includes the cup of FIG. 1 and the securing ring of FIG. 7, without security enhancing fasteners such as screws depicted for the sake of clarity.
Figure 12:
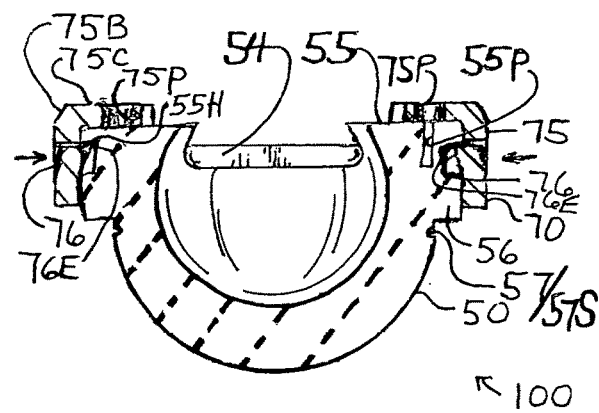
FIG. 12 is a sectional view of the ensemble of FIG. 11, taken along 12-12 in FIG. 11.
Figure 13:
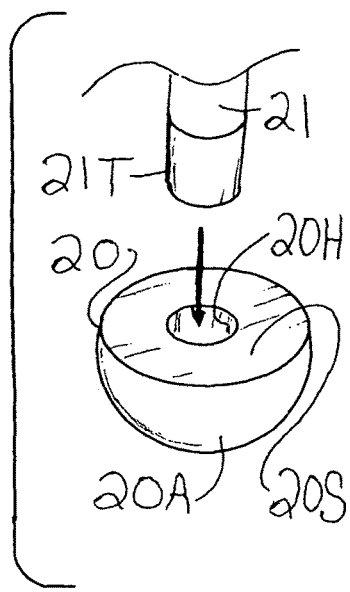
FIG. 13 is an exploded, perspective view of a modular head and stem arrangement for a total joint implant of the invention.
Figure 14:
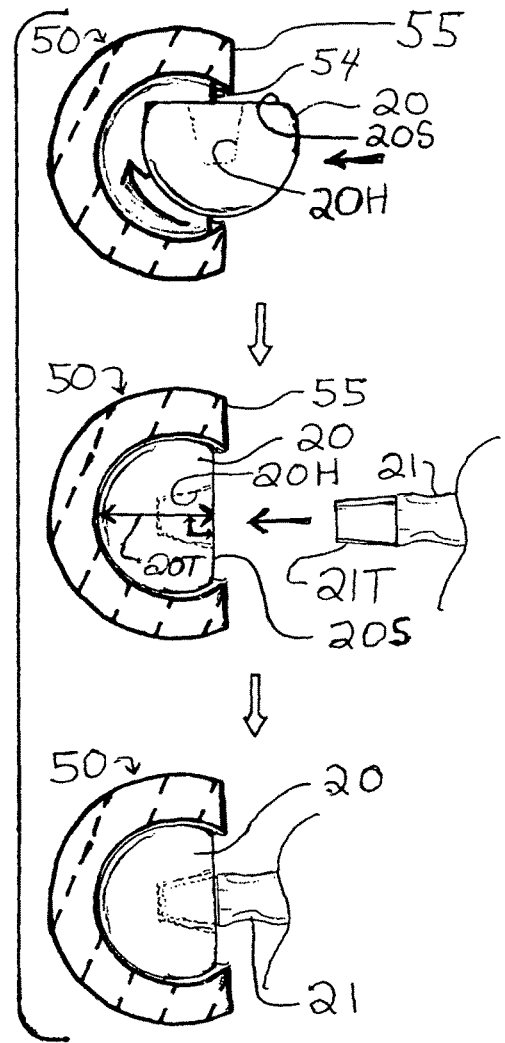
FIG. 14 is a schematic view of another ceramic multi-hooded enarthrodial joint implant cup with a modular head and stem arrangement for a total hip joint implant ensemble of the invention, and its assembly.
Figure 15:
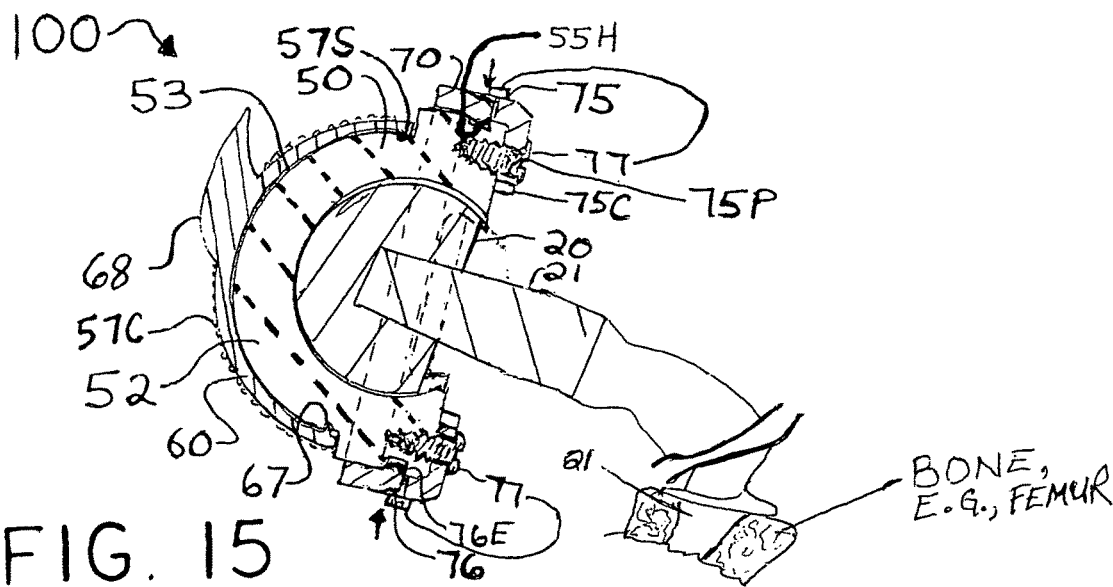
FIG. 15 is a sectional plan view of an ensemble such as that of FIG. 11 and as would be taken along 12-12 in FIG. 11, by which is embraced a ball head of a corresponding implant, here, the ball head of a femoral component for the total hip implant, with a modular head and stem arrangement such as illustratively depicted within FIGS. 13 and 14, two security enhancing fasteners, and a backing shell.
Figure 16:
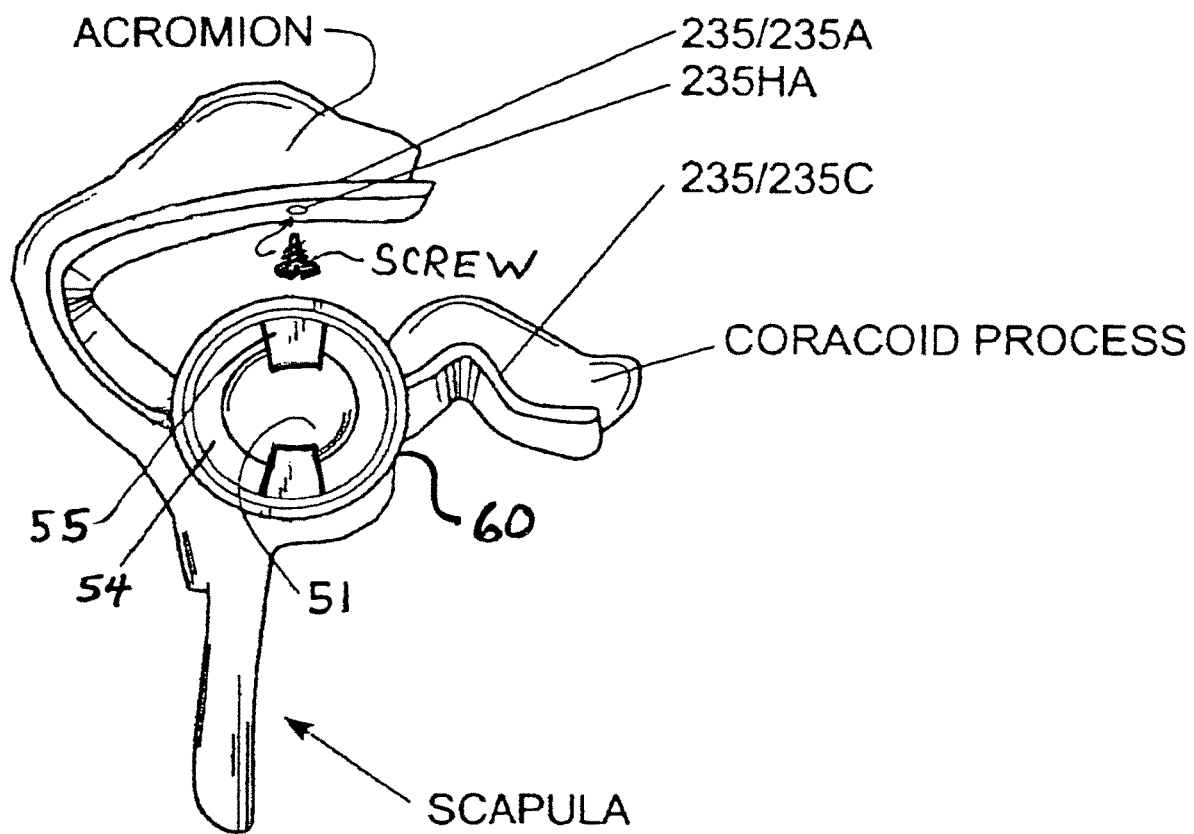
FIG. 16 is "front" view of a another ceramic multi-hooded enarthrodial joint implant cup with a modular head and stem arrangement for a shoulder joint implant of the invention.

The cup 50 made, for example, of the MgO-TTZ according to the Serafin, Jr. et al. '508 patent, includes articular surface 51; body 52; back 53, which may be for facing a backing shell interior when inserted into backing shell 60, or back 53', which is for interfacing resected bone when implanted into the patient; margins 54; and hoods 55, one or more of which may be provided in advance or at the surgical site with ring tab registering side hole 55H and/or pilot hole 55P. The cup 50 also may include circumferential lip 56, which is essentially or to a great extent flat, being essentially or to a great extent parallel with a central axis, and which, with the margins 54 and/or hoods 55, may be level (FIGS. 1-4, 11, 12, 15); be angled at angle "A," say, about from five to twenty degrees, for example, about ten degrees (FIGS. 5, 6); or be absent, wholly or essentially (FIG. 14). The cup 50 may also include fastening aid 57 such as porous coating 57C, which may be most effectively applied to the MgO-TTZ in accordance with Serafin, Jr., U.S. Pat. No. 8,834,576 B1, and Serafin, Jr. et al., Pub. No. US 2010/0076566 A1; circumferential groove 57G into which circumferential ring 57R may be positioned such as by heating to expand the ring 57R, positioning it over and then cooling it to shrink into the groove 57G such as found in Serafin, Jr. et al., U.S. Pat. No. 9,308,674 B1, with the ring 57R able to carry a supply of porous coating 57C; and circumferential slot 57S for engagement through auspices of a locking ring with the backing shell 60 made, for example, of 6-4 ELI titanium alloy in accordance with ASTM F-136 standards, which has complimentary fastening aid 67, here, a circumferential protrusion. The backing shell 60 also may have, among other things, optional cox-comb 68 for insertion into bone stock, notably in the case of a total hip joint replacement implant, and/or have a roughened or the porous coated surface 57C for interfacing with a resected bone surface and promoting bone ingrowth to stabilize the implant. A backing shell 60 for the shoulder may also have arm(s) 235 such as first arm 235A for fastening to the acromion, which may be assisted by providing hole 235HA for a bone screw, and/or second arm 235C for fastening to the coracoid process. Surgical cement such as polymethylmethacrylate may be employed.

The optional securing member 70 made, for example, of cobalt-chrome alloy to ASTM F-799 standards or more demanding standards, and generally in the shape of a ring, includes ring body 72 with marginal arcs 74 and hood braces 75 that include bevel 75B, cover 75C, and perforations 75P, which may take the form of holes. Engagement tabs 76 are biased inwardly, and have edges 76E that may engage the material of the cup 50 about the hood 55 and side hole 55H, which may occur slightly above any lip 56, so as to help secure the ring 70 to the cup 50. In conjunction with or in lieu of the tabs 76 can be side holes 76H. Added fasteners 77 such as screws may be provided for further security, for example, which may be passed through the perforations and/or holes 75P, 76H.

The present invention is thus provided. Various feature(s), part(s), subcombination(s) and combination(s) may be employed with or without reference to other feature(s), part(s), subcombination(s) or combination(s) whereof, and numerous adaptations and modifications can be effected within its spirit, the literal claim scope of which is particularly pointed out as follows:

I claim:

1. An enarthrodial joint implant comprising a ceramic multi-hooded articular cup and an insert having a ceramic head with an articulation surface therefor, wherein:
   the cup includes a head-receiving cup made of ceramic, which is adapted and configured to be fixed when implanted into a patient such that the cup is fixed with respect to the patient directly or with respect to a backing shell in which the cup resides when the backing shell is present and fixed directly to the patient, which has an articular surface upon which the articulation surface of the head can articulate, and which has a margin generally about a hemisphere and two and only two generally opposing hoods that are marginally extended continuations of superior about one-half of cup containment of a sufficient magnitude to reduce an overall dimension of socket outlet to less than a hemisphere, which can embrace and contain the head when the head is inserted into the cup;
   the insert includes a joint head made of ceramic, which has a head body configured generally in a shape of a truncated sphere; a generally spherical articulation surface on the head body; and a truncation to the head body forming a truncated surface in which resides a blind hole for receipt of a trunnion of a stem, wherein:
      the truncated surface is at a central truncation distance extending from a peak of the spherical articulation surface to a center of the truncated surface, wherein the central truncation distance is perpendicular to the truncated surface; and
      the head can be inserted into and retained by the ceramic multi-headed articular cup when the head is inserted into the cup; and
   there is no securing member present for resistance against any likelihood of cracking, fracture, or other failure of the ceramic by application of outwardy displacing force on the hoods.

2. The implant of claim 1, which further comprises the stem having the trunnion, wherein the stem includes an elongate member for insertion into bone; and the trunnion has a male surface inserted into, registering with, and secured by the blind hole of the head.

3. The implant of claim 2, wherein as the at least two generally opposing hoods the cup has two and only two hoods, which oppose one another; the blind hole of the head of the insert is a frustoconical blind hole; the male surface of the trunnion is a frustoconical male surface configured to correspond with the frustoconical blind hole of the head of the insert and provide for a self-locking taper; and the enarthrodial joint is a hip joint.

4. The implant of claim 3, wherein the central truncation distance of the head is about from about from 60% to 85% of the head diameter.

5. The implant of claim 4, wherein at least one of the following features (A-G) is present:
   (A) the frustoconical blind hole of the head has a Morse taper, and the frustoconical male surface of the trunnion has a corresponding Morse taper;
   (B) the ceramic is MgO-TTZ;
   (C) a circumferential outwardly facing groove around the cup, but not the hoods, into which a circumferential ring is positioned;
   (D) an outer backing shell for the cup;
   (E) a bone-interfacing coating;
   (F) a non-magnetic cobalt-chromium-molybdenum alloy as a wrought powder metallurgy product employed to make the stem; and
   (G) the margin and hoods are angled about from five to twenty degrees with respect to a line or plane perpendicular to a central axis of the cup.

6. The implant of claim 4, wherein the ceramic is MgO-TTZ.

7. The implant of claim 2, wherein the central truncation distance of the head is about from about from 60% to 85% of the head diameter.

8. The implant of claim 1, wherein the blind hole of the head of the insert is a frustoconical blind hole; the male surface of the trunnion is a frustoconical male surface configured to correspond with the frustoconical blind hole of the head of the insert and provide for a self-locking taper; and the enarthrodial joint is a hip joint.

9. The implant of claim 8, wherein the central truncation distance of the head is about from about from 60% to 85% of the head diameter.

10. The implant of claim 1, wherein the central truncation distance of the head is about from about from 60% to 85% of the head diameter.

11. A ceramic joint head for an enarthrodial joint implant having a ceramic double-hooded articular cup, which comprises a head body made of ceramic and configured generally in a shape of a truncated sphere; a generally spherical articulation surface on the head body; and a truncation to the head body forming a truncated surface in which resides a blind frustoconical hole for receipt of a trunnion of a stem, wherein:
   the truncated surface is at a central truncation distance extending from a peak of the spherical articulation surface to a center of the truncated surface, wherein the central truncation distance is perpendicular to the truncated surface;
   the joint head is configured for insertion into and retention by the ceramic double-hooded articular cup, which is adapted and configured to be fixed when implanted into a patient such that the cup is fixed with respect to the patient directly or with respect to a backing shell in which the cup resides when the backing shell is present and fixed directly to the patient, which has an articular surface upon which the articulation surface of the joint head can articulate, and which has a margin generally about a hemisphere and two and only two generally opposing hoods that are marginally extended continuations of superior about one-half of cup containment of a sufficient magnitude to reduce an overall dimension of socket outlet to less than a hemisphere, which can embrace and contain the joint head when the joint head is inserted into the cup;
   the enarthrodial joint is a hip joint; and
   there is no securing member present for resistance against any likelihood of cracking, fracture, or other failure of the ceramic by application of outwardy displacing force on the hoods.

12. The insert of claim 11, wherein the ceramic is MgO-TTZ; and
   the central truncation distance is about from about from 65% to 80% of the head diameter.

13. The insert of claim 12, wherein the central truncation distance is about from 70% to 75% of the head diameter.

14. A ceramic double-hooded articular cup for an enarthrodial joint implant, which comprises a head-receiving cup made of ceramic, which is adapted and configured to be fixed when implanted into a patient such that the cup is fixed with respect to the patient directly or with respect to a backing shell in which the cup resides when the backing shell is present and fixed directly to the patient, which has an articular surface upon which a head of a joint can articulate, and which has a margin generally about a hemisphere and two and only two generally opposing hoods that are marginally extended continuations of superior about one-half of cup containment of a sufficient magnitude to reduce an overall dimension of socket outlet to less than a hemisphere, which can embrace and contain the head when the head is inserted into the cup, wherein:
   the enarthrodial joint is a hip joint; and
   there is no securing member present for resistance against any likelihood of cracking, fracture, or other failure of the ceramic by application of outwardly displacing force on the hoods.

15. The cup of claim 14, wherein the ceramic is MgO-TTZ.

\* \* \* \* \*